United States Patent [19]

Mercker et al.

[11] Patent Number: 6,093,677
[45] Date of Patent: Jul. 25, 2000

[54] CATALYST FOR DEHYDROGENATING 1,4-BUTANEDIOL TO γ-BUTYROLACTONE

[75] Inventors: Hans Jochen Mercker, Mannheim; Frank-Friedrich Pape, Kleinniedesheim; Joachim Simon, Mannheim; Andreas Henne, Neustadt; Michael Hesse, Worms; Ulrich Köhler, Mannheim; Roman Dostalek, Römerberg; Cristina Freire Erdbrügger, Freinsheim; Detlef Kratz, Heidelberg, all of Germany

[73] Assignee: BASF Aktiengesellschaft, Ludwigshafen, Germany

[21] Appl. No.: 09/323,919

[22] Filed: Jun. 2, 1999

Related U.S. Application Data

[62] Division of application No. 08/923,553, Sep. 4, 1997, Pat. No. 5,955,620.

[30] Foreign Application Priority Data

Sep. 5, 1996 [DE] Germany ............... 196 36 066

[51] Int. Cl.⁷ ............... B01J 23/72; B01J 23/70
[52] U.S. Cl. ............ 502/345; 502/340; 502/344
[58] Field of Search ............ 502/344, 345, 502/340

[56] References Cited

U.S. PATENT DOCUMENTS

| | | | |
|---|---|---|---|
| 4,268,695 | 5/1981 | Lange et al. | 568/864 |
| 4,652,685 | 3/1987 | Cawse et al. | 568/864 |
| 4,940,805 | 7/1990 | Fischer et al. | 549/326 |
| 5,591,873 | 1/1997 | Bankmann et al. | 502/244 |
| 5,646,307 | 7/1997 | Pinkos et al. | 549/295 |
| 5,801,114 | 9/1998 | Durand et al. | 502/302 |

FOREIGN PATENT DOCUMENTS

| | | |
|---|---|---|
| 584 408 | 3/1994 | European Pat. Off. . |
| 699 945 | 12/1940 | Germany . |
| 1066979 | 4/1967 | United Kingdom . |

OTHER PUBLICATIONS

Chem Abst. Derwent J6 1246 173 A, 1986.
Chem Abst. Derwent J0 2255 668 A, 1990.
Ulmanns Enzyklopadie der technischen Chemie, 3$^{rd}$ Ed. vol. 4, pp. 802 and 803, 1953.
Bartok et al., Acta Chim. Acad. Sci. Hung., vol. 100, No. 1–4, 1979, pp. 203–210.
Ullmann's Ency. of Indus. Chem.—5$^{th}$ Ed., vol. A4, 1985, pp. 496–497.

*Primary Examiner*—Steven P. Griffin
*Assistant Examiner*—Michael Rhee
*Attorney, Agent, or Firm*—Keil & Weinkauf

[57] ABSTRACT

A process for dehydrogenating 1,4-butanediol to γ-butyrolactone in the gas phase in the presence of a copper-containing catalyst, wherein the catalyst contains 4–40% by weight of copper and 0–5% by weight of $Na_2O$, based on the total weight of the catalyst, on a carrier consisting of 80–100% by weight of $SiO_2$ and 0–20% by weight of CaO.

4 Claims, No Drawings

CATALYST FOR DEHYDROGENATING 1,4-BUTANEDIOL TO γ-BUTYROLACTONE

This is a division of application Ser. No. 08/923,553, filed Sep. 4, 1997, now U.S. Pat. No. 5,955,620.

The invention relates to a process for dehydrogenating, 4-butanediol to γ-butyrolactone in the gas phase.

A number of processes for the catalytic dehydrogenation of 1,4-butanediol to γ-butyrolactone is known.

Processes for preparing γ-butyrolactone from 1,4-butanediol are described in Ullmanns Enzyklopädie der technischen Chemie, Urban & Schwarzenberg, Munich, 3rd edition 1953, Volume 4, pages 802 and 803. In the liquid-phase process, hot liquid 1,4-butanediol is pumped under atmospheric pressure into a furnace which is packed with copper catalyst (Cu on silica gel) and heated to about 200° C. In the vapor-phase process, the butanediol vapors are circulated with hydrogen under atmospheric pressure over a catalyst (Cu on pumice) which is heated to about 230–250° C. The resulting crude butyrolactone contains water and traces of butyraldehyde in addition to tetrahydrofuran and its isomers. The disadvantages of the process are the relatively poor dehydrogenating action of the catalyst used, and the large amount of byproducts formed.

JP-A 61-246173 describes the use of Cu/Cr/Mn catalysts and Cu/Cr/Zn catalysts for dehydrogenating 1,4-butanediol. The catalyst is obtained, for example, from $CuCr_2O_4$ and $ZnCr_2O_4$.

JP-A 02-255668 discloses the use of Cu/Zn catalysts for the gas-phase dehydrogenation of 1,4-butanediol.

The Cu/Cr catalysts are elaborate to prepare and difficult to employ for environmental reasons because of the use of chromium compounds. Cu/Zn catalysts usually have inadequate useful lives.

It is an object of the present invention to provide a process for dehydrogenating 1,4-butanediol to γ-butyrolactone which avoids the disadvantages of known processes.

We have found that this object is achieved by a process for dehydrogenating 1,4-butanediol to γ-butyrolactone in the gas phase in the presence of a copper-containing catalyst, wherein the catalyst contains 4–40% by weight of copper and 0–5% by weight of $Na_2O$, based on the total weight of the catalyst, on a carrier consisting of 80–100% by weight of $SiO_2$ and 0–20% by weight of CaO.

Use of the catalyst according to the invention is advantageous for industrial, economic and ecological reasons. The catalyst employed according to the invention displays excellent activity despite the intrinsically low dehydrogenating action of copper. Compared with known copper catalysts based on silica gel and used for synthesizing γ-butyrolactone in a liquid procedure, the catalyst according to the invention is less prone to coking and has a longer useful life.

Catalyst

The catalyst according to the invention for dehydrogenating 1,4-butanediol to γ-butyrolactone contains 4–40% by weight, preferably 4–32% by weight, of copper and 0–5% by weight, preferably 0–2% by weight, of $Na_2O$, based on the total weight of the catalyst, on a carrier consisting of 80–100% by weight, preferably 90–100% by weight, of $SiO_2$ and 0–20% by weight, preferably 0–10% by weight, of CaO.

The surface area of copper on the carrier is preferably more than 5 $m^2/g$, particularly preferably more than 10 $m^2/g$, and is in particular in the range above 10 $m^2/g$ up to 50 $m^2/g$.

The copper dispersion is preferably more than 10%, particularly preferably more than 20%, and is in particular in the range above 20% up to 50%.

The catalyst according to the invention preferably has an average copper particle size of less than 200 nm, particularly preferably in the range from 5 to 150 nm, in particular in the range of from 10 to 100 nm.

The surface area of copper is determined by heating an accurately weighed amount of catalyst after flushing with helium for one hour to 200° C. under reduced pressure and subsequently reducing with $H_2$ over a period of 16 hours. After reduction is complete, the pressure is reduced again, the sample is allowed to cool to 35° C., and the oxygen chemisorption is determined by a volumetric sorption method (measurement of at least four defined pressure points). Assuming that in each case two copper atoms react with one oxygen atom, it is possible to determine therefrom the surface area of copper via the space required by the copper atoms. This makes comparisons of catalysts very easy.

The copper dispersion can be calculated from the surface area of copper and the concentration of copper present in the catalyst. This term means the ratio of the number of copper atoms on the surface of the copper particles, i.e. the available copper atoms, to the total number of copper atoms present in the copper crystallites. This total number is obtained from the copper content in the catalyst, which can be obtained by simple chemical analysis. This ratio is expediently standardized.

The size of the copper crystallites can also be determined directly. Suitable for this is, for example, transmission electron microscopy. The samples are fixed in poly(methyl methacrylate), and a thin section is made (ultramicrotomy). Magnifications of 500,000 permit even very small particles sizes of 1 nm to be determined satisfactorily with this precise method. The phase of the particles can be determined using EDXS Energy Dispersive X-Ray Spectroscopy) or SAD (Selected Area Diffraction).

In one embodiment of the invention, the catalyst contains 16–32% by weight of copper, based on the total weight of the catalyst, on an $SiO_2$ carrier with a surface area of copper of more than 25 $m^2/g$ and a copper dispersion of more than 20%. The amount of copper in this case is preferably about 20% by weight.

In one embodiment of the invention, the catalyst contains 4–16% by weight of copper and 0.5–1% by weight of $Na_2O$, based on the total weight of the catalyst, on a carrier consisting of 90–95% by weight of $SiO_2$ and 5–10% by weight of CaO, with a surface area of copper of more than 10 $m^2/g$ and a copper dispersion of more than 20%. The copper content is preferably about 8–9% by weight, the $Na_2O$ content is 0.5–1% by weight and the CaO content in the carrier is about 7% by weight.

The catalyst carrier is preferably a highly porous carrier with a specific surface area of more than 100 $m^2/g$. $SiO_2$ is used as carrier, with or without addition of CaO, and is preferably in the form of beads, pellets, tablets or rings, so that the catalyst can be employed as fixed bed. The carrier is preferably employed in the form of pellets with a thickness of about 4–5 mm or in the form of beads with a diameter of 3–5 mm, It is possible to use, for example, $SiO_2$ containing wollastonite, in which case the wollastonite content is, in particular, about 7% of the weight of the carrier.

Preparation of the Catalyst

The catalyst used according to the invention can be prepared by impregnating the carrier consisting of $SiO_2$, with or without CaO, with aqueous ammoniacal copper carbonate solution, with or without aqueous sodium nitrate solution.

The impregnation takes place in the supernatant solution over the course of 15 minutes. The impregnated carriers are then dried at 120° C. for 5 hours and subsequently calcined at 350° C. for 2 hours. The impregnation and calcination steps can be repeated several times in order to achieve a required copper content and, where appropriate, additional $Na_2O$ content. The copper content and the $Na_2O$ content of the impregnation solutions are adjusted so that the required copper content on the catalyst is obtained after impregnation one or more times. Copper carbonate solution and sodium nitrate solution can be used for the impregnation simultaneously or successively. After the calcination, the catalyst contains 5–50% by weight of CuO, equivalent to 4–40% by weight of Cu, preferably 5–40% by weight of CuO, equivalent to 4–32% by weight of Cu, based on the complete catalyst. Before the reaction, the catalyst is reduced in a stream of hydrogen so that elemental copper is present in the catalyst ready for use in the reaction.

Dehydrogenation

The dehydrogenation of 1,4-butanediol to γ-butyrolactone takes place in the gas phase at from 150 to 300° C., preferably 180 to 260° C., particularly preferably 190 to 230° C. The dehydrogenation is carried out under an absolute pressure of from 1 to 40 bar, preferably 1 to 10 bar, particularly preferably 1 to 2 bar, in particular about 1 bar.

The catalyst is preferably employed for this purpose in the form of beads, pellets, tablets or rings as fixed bed.

The process according to the invention can be carried out batchwise or continuously, preferably continuously. In the continuous procedure, the space velocity is preferably 0.2–20 kg, particularly preferably 0.5–10 kg, in particular 0.5–7.5 kg, of 1,4-butanediol per kg of copper per hour.

The dehydrogenation according to the invention is preferably carried out in the presence of free hydrogen. The free hydrogen can be added for this purpose, or the free hydrogen produced during the dehydrogenation can be employed. As a rule, a gas containing free hydrogen is fed in at the start of the dehydrogenation in order to reduce the catalyst in the stream of hydrogen. Then, after the dehydrogenation has started up, some of the hydrogen produced is returned to the dehydrogenation.

In a preferred embodiment of the process according to the invention, 1,4-butanediol is converted into the gas phase in a vaporizer and passed, with a carrier gas containing free hydrogen, through a reactor which contains the catalyst; γ-butyrolactone is condensed out and discharged downstream of the reactor, and some of the carrier gas is discharged and the remaining carrier gas is returned as circulating gas.

Any suitable vaporizer can be used to vaporize 1,4-butanediol. Hydrogen can be obtained from the discharged carrier gas and be employed for other chemical reactions. The resulting γ-butyrolactone, which contains very small amounts of 1,4-butanediol, can be isolated and purified after the reaction by conventional methods, for example by distillation or extraction. Any unreacted starting materials, in particular 1,4-butanediol, can moreover be returned to the reaction.

The invention is illustrated by means of examples hereinafter.

Test Apparatus

The catalyst prepared by the process described above is packed into an electrically heated cylindrical glass reactor with a volume of 300 ml which has two upstream vaporizers which are packed with Raschig rings and are heated to 250° C. and 270° C. respectively. 1,4-Butanediol is fed by a piston pump into the first vaporizer. Downstream of the reactor are 3 Dimroth condensers in which the reaction product, γ-butyrolactone, is condensed out. 50 l (STP)/h of reaction gas are returned by a circulating gas pump, with excess reaction gas being discharged. At the start of the reaction, the catalyst is reduced in the glass reactor in a stream of hydrogen, with or without nitrogen, which is fed in as fresh gas stream.

Preparation of γ-butyrolactone

EXAMPLE 1

At a reaction temperature of 210° C., 42 g/h of 1,4-butanediol are passed over 250 g of a catalyst which is present in the form of pellets with a diameter of 4 to 5 mm in the reactor. The catalyst contains 12% by weight of CuO (9.6% by weight of Cu) and 0.8% by weight of $Na_2O$, based on the complete catalyst, on 93% by weight of $SiO_2$ with 7% by weight of CaO as carrier. The surface area of copper is more than 10 $m^2/g$, and the copper dispersion is more than 20%. The space velocity is 1.75 kg of 1,4-butanediol per kg of copper per hour. With a conversion of more than 99.9%, the selectivity for γ-butyrolactone is 98%. The conversion and selectivity remain at the same level for at least one week. No carbon deposits are detected on the catalyst after removal from the apparatus.

EXAMPLE 2

At a reaction temperature of 210° C., 125 g/h of 1,4-butanediol are passed over 200 g of a catalyst which is present in the form of pellets with a diameter of 4 to 5 mm in the reactor. The catalyst contains 12% by weight of CuO (9.6% by weight of Cu) and 0.8% by weight of $Na_2O$, based on the complete catalyst, on 93% by weight of $SiO_2$ with 7% by weight of CaO as carrier. The space velocity is 5.3 kg of 1,4-butanediol per kg of copper per hour. The conversion is more than 99.7%, and the selectivity for γ-butyrolactone is 99%. The conversion and selectivity remain at the same level for at least one week. No carbon deposits are detected on the catalyst after removal from the apparatus.

EXAMPLE 3

At a reaction temperature of 210° C., 42 g/h of 1,4-butanediol are passed over 250 g of a catalyst which is present in the form of beads with a diameter of 3 to 5 mm in the reactor. The catalyst contains 25% by weight of CuO (20% by weight of Cu) on $SiO_2$ as carrier. The surface area of copper is more than 25 $m^2/g$ and the copper dispersion is more than 20%. The space velocity is 0.8 kg of 1,4-butanediol per kg of copper per hour. The conversion is at least 99.5%, and the selectivity for γ-butyrolactone is 98%. The conversion and selectivity remain at the same level for at least 2 weeks. No carbon deposits are detected on the catalyst after removal from the apparatus.

EXAMPLE 4

At a reaction temperature of 210° C., 125 g/h of 1,4-butanediol are passed over 250 g of a catalyst which is present in the form of beads with a diameter of 3 to 5 mm in the reactor. The catalyst contains 25% by weight of CuO (20% by weight of Cu) on $SiO_2$ as carrier. The space velocity is 2.5 kg of 1,4-butanediol per kg of copper per hour. The conversion is at least 99.5%, and the selectivity for γ-butyrolactone is 97–98%. The conversion and selectivity remain at the same level for at least one week. No carbon deposits are detected on the catalyst after removal from the apparatus.

We claim:

1. A catalyst for dehydrogenating 1,4-butanediol to γ-butyrolactone, comprising 4–40% by weight of copper and 0–5% by weight of $Na_2O$, based on the total weight of the catalyst, on a carrier consisting of 90–95% by weight of $SiO_2$ and 5–10% by weight of CaO, with a surface area of copper of more than 10 $m^2/g$ and a copper dispersion of more than 20%.

2. The catalyst of claim 1, wherein the catalyst contains 16–32% by weight of copper, based on the total weight of the catalyst, with a surface area of copper of more than 25 $m^2/g$.

3. The catalyst of claim 1, wherein the catalyst contains 4–16% by weight of copper and 0.5–1% by weight of $Na_2O$, based on the total weight of the catalyst.

4. The catalyst of claim 1, wherein the carrier has a specific surface area of more than 100 $m^2/g$.

* * * * *